US009162010B2

(12) United States Patent
Lenarz et al.

(10) Patent No.: US 9,162,010 B2
(45) Date of Patent: Oct. 20, 2015

(54) DRUG ELUTING COCHLEAR IMPLANTS

(75) Inventors: Thomas Lenarz, Hannover (DE);
Klaus-Peter Schmitz,
Rostock-Warnemünde (DE); Detlef Behrend, Rostock-Warnemünde (DE);
Katrin Sternberg, Rostock (DE); Simon Williams, Sherborn, MA (US); David Martin, Arlington, MA (US)

(73) Assignee: Tepha, Inc., Lexington, MA (US)

( * ) Notice: Subject to any disclaimer, the term of this patent is extended or adjusted under 35 U.S.C. 154(b) by 0 days.

(21) Appl. No.: 13/284,287

(22) Filed: Oct. 28, 2011

(65) Prior Publication Data

US 2012/0283666 A1 Nov. 8, 2012

Related U.S. Application Data

(60) Provisional application No. 61/411,631, filed on Nov. 9, 2010, provisional application No. 61/530,698, filed on Sep. 2, 2011.

(51) Int. Cl.
| | |
|---|---|
| *A61K 9/00* | (2006.01) |
| *A61L 31/10* | (2006.01) |
| *A61L 27/34* | (2006.01) |
| *A61L 27/54* | (2006.01) |
| *A61N 1/36* | (2006.01) |
| *A61M 31/00* | (2006.01) |
| *A61L 31/08* | (2006.01) |

(52) U.S. Cl.
CPC ............... *A61L 27/34* (2013.01); *A61L 27/54* (2013.01); *A61N 1/36032* (2013.01); *A61K 9/0024* (2013.01); *A61L 31/08* (2013.01); *A61L 31/10* (2013.01); *A61L 2300/258* (2013.01); *A61L 2300/406* (2013.01); *A61L 2300/41* (2013.01); *A61L 2300/416* (2013.01); *A61M 31/002* (2013.01)

(58) Field of Classification Search
CPC ... A61K 9/0024; A61M 31/002; A61L 31/08; A61L 4/10
See application file for complete search history.

(56) References Cited

U.S. PATENT DOCUMENTS

| | | | |
|---|---|---|---|
| 5,811,272 A | 9/1998 | Snell | |
| 6,245,537 B1 | 6/2001 | Williams | |
| 6,309,410 B1 | 10/2001 | Kuzma | |
| 6,316,262 B1 | 11/2001 | Huisman | |
| 6,323,010 B1 | 11/2001 | Skraly | |
| 6,548,569 B1 | 4/2003 | Williams | |
| 6,555,123 B2 | 4/2003 | Williams | |
| 6,585,994 B2 | 7/2003 | Williams | |
| 6,610,764 B1 | 8/2003 | Martin | |
| 6,623,748 B2 | 9/2003 | Clokie | |
| 6,828,357 B1 | 12/2004 | Martin | |
| 6,838,493 B2 | 1/2005 | Williams | |
| 6,867,248 B1 | 3/2005 | Martin | |
| 6,878,758 B2 | 4/2005 | Martin | |
| 6,905,987 B2 | 6/2005 | Noda | |
| 7,025,980 B1 | 4/2006 | Williams | |
| 7,244,442 B2 | 7/2007 | Williams | |
| 2003/0211131 A1 | 11/2003 | Martin | |
| 2004/0039437 A1* | 2/2004 | Sparer et al. ................ | 623/1.15 |
| 2005/0025809 A1 | 2/2005 | Hasirci | |
| 2006/0020318 A1 | 1/2006 | Lenarz | |
| 2007/0135929 A1 | 6/2007 | Williams | |
| 2007/0213799 A1 | 9/2007 | Jolly | |
| 2009/0012604 A1* | 1/2009 | Schmitz et al. ............. | 623/1.42 |
| 2009/0093872 A1 | 4/2009 | Schmitz | |
| 2009/0292237 A1 | 11/2009 | Overstreet | |
| 2010/0160891 A1 | 6/2010 | Tipton | |

FOREIGN PATENT DOCUMENTS

| | | |
|---|---|---|
| WO | 9932536 | 7/1999 |
| WO | 0056376 | 9/2000 |
| WO | 2005007195 | 1/2005 |
| WO | 2005020825 | 3/2005 |
| WO | 2007092418 | 8/2007 |
| WO | 2009006538 | 1/2009 |
| WO | 2009158724 | 12/2009 |
| WO | 2010017014 | 2/2010 |

OTHER PUBLICATIONS

Peschel et al., Growth of Kertatinocytes on Porous Films of Poly (3-Hydroxybutyrate) and Poly (4-Hydroxybutyrate) Blended with Hyaluronic Acid and Chitosan, Oct. 15, 2007,Journal of Biomedical Materials Research Part A, Journal of Biomedical Materials Research Part A, vol. 85A, Issue 4, pp. 1072-1081.*
Hori, et al., "Chemical synthesis of high molecular weight poly (3-hydroxybutyrate-co-4-hydroxybutyrate" , Polymer, 36:4703-4705 (1995).
Martin, et al., "Medical Applications of Poly-4-hydroxybutyrate: A Strong Flexible Absorbable Biomaterial" , Biochem. Eng. J., 16:97-105 (2003).
Steinbüchel, et al., "Diversity of Bacterial Polyhydroxyalkanoic Acids" , FEMS Microbial. Lett., 128:219-228 (1995).
Williams, et al., "Applications of PHAs in Medicine and Pharmacy, in Biopolymers" , Polyesters, III, 4:91-127 (2002).

* cited by examiner

*Primary Examiner* — Ali Soroush
(74) *Attorney, Agent, or Firm* — Pabst Patent Group LLP

(57) ABSTRACT

Drug delivery systems and biocompatible coatings for use with implantable stimulation devices such as cochlear implants have been developed. These drug delivery systems and coatings comprise polyhydroxyalkanoate (PHA) polymers and copolymers. The drug delivery systems may be used to deliver pharmacologically active substances, for example, directly from a cochlear implant to the inner ear. The coatings can impart lubricity to cochlear devices for ease of insertion of the electrodes. In the preferred embodiment, the drug delivery system comprises a polyhydroxyalkanoate polymer, and in the most preferred embodiment, the PHA polymer comprises poly(4-hydroxybutyrate) (P(4HB)) or copolymer thereof. A particularly preferred embodiment is where the silicone sheath of the cochlear implant electrodes has been surface modified, and coated with P(4HB), and the P(4HB) either contains a pharmacologically active substance or has been coated with such a substance.

13 Claims, 3 Drawing Sheets

DRUG ELUTING COCHLEAR IMPLANTS

CROSS REFERENCE TO RELATED APPLICATIONS

This application claims priority to U.S. Ser. No. 61/411,631 filed Nov. 9, 2010, and U.S. Ser. No. 61/530,698 filed Sep. 2, 2011, both of which are incorporated by reference in their entirety.

FIELD OF THE INVENTION

The present invention generally relates to implantable stimulation devices, for example, cochlear implants, and more specifically to drug eluting implantable stimulation devices. The devices include polyhydroxyalkanoate polymers and copolymers able to elute pharmacologically active substances particularly from a cochlear implant into the inner ear.

BACKGROUND OF THE INVENTION

There is a need for implantable stimulation devices, such as cochlear implants, that can elute pharmacologically active substances following implantation. Such devices could, for example, improve the signal quality of a cochlear implant.

For many patients that are profoundly deaf, their deafness is a result of the loss or absence of hair cells in the cochlea that are necessary to transduce acoustic signals (e.g. sound energy) into auditory nerve impulses. These patients have sensorineural hearing loss (as opposed to conductive hearing loss that can often be treated with conventional hearing aids). Without hair cells, patients with sensorineural hearing loss are unable to generate auditory nerve impulses directly from sounds.

Many cochlear implants have been developed to treat patients with sensorineural hearing loss. These implants are capable of directly stimulating auditory nerve fibers, therein bypassing the hair cells, and producing the perception of sound in the brain and thus some sense of hearing. Such implants normally comprise a set of electrodes (an electrode array) that are implanted into the cochlea. These electrodes are designed to respond to external electrical stimuli, and in turn transmit these impulses to the ganglion cells and the auditory nerve fibers. In an ideal situation, the electronic circuitry combined with the electrodes of the cochlear implant would separate an acoustic signal into narrow bands of frequencies, and these frequency bands would be conveyed selectively to the auditory nerve cells normally responsible for transmitting those frequencies to the brain.

The electrode array of the cochlear implants is generally implanted in the scala tympani, one of three ducts of the spiral shaped cochlea, for best results. The array usually consists of a thin, elongated, flexible carrier containing six to thirty separate electrode contacts, and is inserted by the surgeon into the scala tympani duct. When electrical impulses are delivered from the individual electrodes to tissues and fluids in close proximity, spiral ganglion cells and their auditory nerve fibers create action potentials.

Despite tremendous success in restoring sound sensation to patients that are profoundly deaf with cochlear implants, performance of the implants can often be suboptimal due to (i) apoptosis and/or necrosis of nervous tissue resulting from the trauma of inserting the electrode array, and (ii) a rise in electrode impedance post-surgery that is due to the encapsulation of the electrode array by the growth of a fibrous membrane which reduces the efficiency of electrical stimulation.

Efforts to address these issues include a single intraoperative intracochlear application of corticosteroids during cochlear implantation to reduce impedances at the electrode contacts, and surface patterning of the electrode array to reduce growth of cells on the implant surface (see US Patent Application No. 20060020318 to Lenarz, et al., "Patterning of the surface of implantable devices for tissue growth management"). In addition, U.S. Pat. No. 6,309,410 to Kuzma, et al. describes a cochlear electrode with an incorporated drug delivery channel for application of drugs, and US Patent Application No. 20070213799 to Jolly, et al. describes cochlear implants with material in areas of the implant adapted to elute drug.

There is thus a need to develop materials that can minimize the force required to insert an electrode array into the cochlea, and thereby limit the trauma to the spiral ganglion cells.

There is also a further need to develop technology that allows pharmacologically active substances to be delivered to the inner ear after cochlear implantation, but without surgery. Delivery of pharmacologically active substances in the inner ear after cochlear implantation could (a) provide therapeutic treatment for trauma resulting from insertion of the electrode array, and (b) decrease fibrous growth. In addition, infection could be prevented or treated locally with antibiotics.

It is an object of the present invention to provide polyhydroxyalkanoate (PHA) coatings for implantable stimulation devices, including cochlear implants, wherein the coating provides the electrode with good lubricity to minimize trauma to tissues.

It is a further object of the present invention to provide implantable stimulation devices, including cochlear implants, which can deliver pharmacologically active substances, and comprise PHA polymers and copolymers.

It is another object of the present invention to provide PHA polymer and copolymer drug delivery systems for implantable stimulation devices that can be used to make cochlear implants with excellent physical and mechanical properties and biocompatibility.

SUMMARY OF THE INVENTION

Drug delivery systems and biocompatible coatings for use with implantable stimulation devices such as cochlear implants have been developed. These drug delivery systems and coatings comprise polyhydroxyalkanoate (PHA) polymers and copolymers. The drug delivery systems may be used to deliver pharmacologically active substances, for example, directly from a cochlear implant to the inner ear. The active substances can be antibiotics, anti-inflammatory drugs, anti-apoptosis agents, anti-oxidants, neurotrophic factors, gene therapy agents, or other substances that can prevent, for example, fibrous tissue formation, infection, and apoptosis and/or necrosis of nervous tissue. The coatings impart good lubricity to cochlear devices for ease of insertion of the electrodes. In the preferred embodiment, the drug delivery system comprises a polyhydroxyalkanoate polymer, and in the most preferred embodiment, the PHA polymer comprises poly(4-hydroxybutyrate) (P(4HB)) or copolymer thereof. A particularly preferred embodiment is where the silicone sheath of the cochlear implant electrodes has been surface modified and coated with P(4HB), and the P(4HB) either contains a pharmacologically active substance or has been coated with such a substance.

BRIEF DESCRIPTIONS OF THE DRAWINGS

Figure 4:
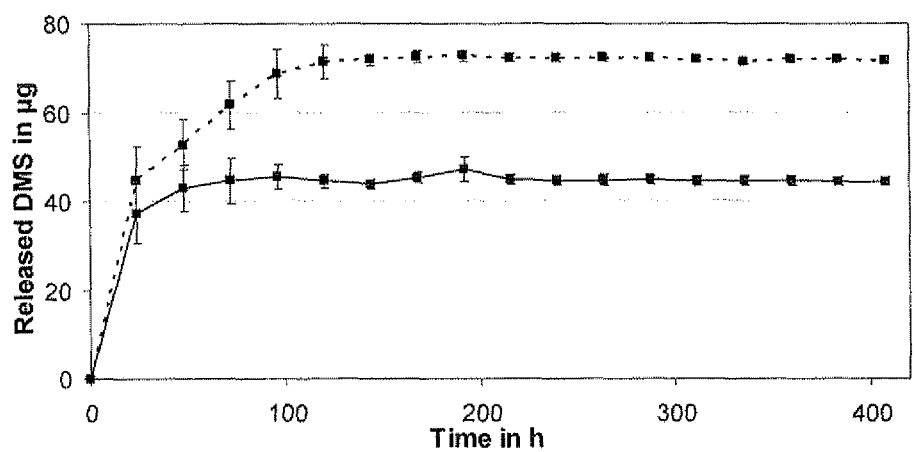

FIG. 4 is a graph of in vitro DMS release from DMS-containing P(4HB) coatings on silicone discs with a diameter of 6 mm in isotonic NaCl solution at 37° C. under quasi-stationary conditions. Silicone with P(4HB) 85/15% (w/w) (—■—); Silicone with P(4HB) 70/30% (w/w) (—■—).

Figure 5:
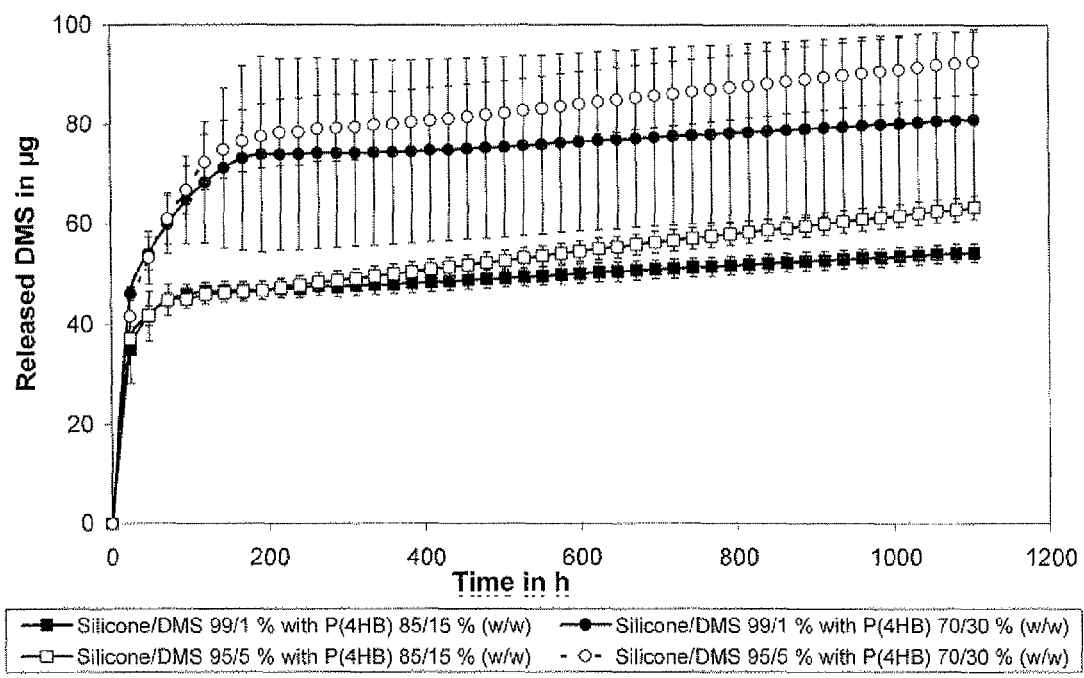

FIG. 5 is a graph of in vitro drug release from DMS-containing silicone carriers with polymer drug coatings under quasi-stationary conditions.

DETAILED DESCRIPTION OF THE INVENTION

I. Definitions

"Poly(4-hydroxybutyrate)" as generally used herein means a homopolymer comprising 4-hydroxybutyrate units. It may be referred to herein as P(4HB) or TephaFLEX® biomaterial (manufactured by Tepha, Inc., Lexington, Mass.).

"Polylactide or polylactic acid" as generally used herein means a homopolymer of lactic acid units. It may be referred to herein as PLLA, PLA, or DL-PLA. (PLLA is manufactured by Boehringer-Ingelheim Pharma, Germany.)

"Copolymers of poly(4-hydroxybutyrate)" as generally used herein means any polymer comprising 4-hydroxybutyrate with one or more different hydroxy acid units.

"Blend" as generally used herein means a physical combination of different polymers, as opposed to a copolymer comprised of two or more different monomers chemically coupled together.

"Tensile modulus" is the ratio of stress to strain for a given material within its proportional limit.

"Toughness" means a property of a material by virtue of which it can absorb energy; the actual work per unit volume or unit mass of material that is required to rupture it. Toughness is usually proportional to the area under the load-elongation curve such as the tensile stress-strain curve. (Rosato's Plastics Encyclopedia and Dictionary, Oxford Univ. Press, 1993.)

"Elongation" or extensibility of a material means the amount of increase in length resulting from, as an example, the tension to break a specimen. It is expressed usually as a percentage of the original length. (Rosato's Plastics Encyclopedia and Dictionary, Oxford Univ. Press, 1993.)

"Molecular weight" as used herein, unless otherwise specified, refers to the weight average molecular weight (Mw), not number average molecular weight (Mn), and is measured by GPC relative to polystyrene standards.

"Absorbable" as generally used herein means the material is broken down in the body and eventually eliminated from the body within five years.

"Biocompatible" as generally used herein means the biological response to the material or device being appropriate for the device's intended application in vivo. Any metabolites of these materials should also be biocompatible.

"Cytotoxicity" is measured using a rapid, standardized test that is very sensitive and inexpensive, to determine if the materials in a medical device contain significant quantities of harmful extractables and their effect on cellular components. Testing is required for all types of medical devices. Cellular toxicity is covered in ISO 10993-5. In the agar overlay method, a thin layer of agar media is placed on top of a monolayer of L929 cells, and a sample is placed on top of the agar media, then incubated. For the MEM elution method, an extract of the sample into minimum essential medium (MEM) is placed in contact with the monolayer of L929 cells and then incubated. In both methods the cells are scored for cytopathic effect.

II. Compositions

Methods have been developed to produce implantable stimulation devices comprising PHA coatings. These coatings can also incorporate pharmacologically active substances. These methods have been applied to medical devices, such as cochlear implants.

A. Polymers

The processes described herein can typically be used to apply coatings of polyhydroxyalkanoate polymers, and more preferably poly(4-hydroxybutyrate) (P(4HB)) or a copolymer thereof, to implantable stimulation devices, and more specifically, cochlear implants. Copolymers include P(4HB) with 3-hydroxybutyrate, and P(4HB) with glycolic acid monomer. P(4HB) and copolymers thereof can be obtained from Tepha, Inc. of Lexington, Mass. Preferred PHA polymers have a weight average molecular weight (Mw) suitable for solvent processing, and more preferably a Mw of 50,000 to 1,200,000, and even more preferably 50,000 to 800,000. If desired, the PHA polymer may be blended with another PHA polymer prior to applying it to an implantable stimulation device, or blended with a non-PHA material, including other absorbable biocompatible polymers (for example, PLA), dyes and pharmacologically active substances (such as drug molecules).

Poly(4-hydroxybutyrate) (P(4HB)) and copolymers thereof can be produced using transgenic fermentation methods, see, for example, U.S. Pat. No. 6,548,569 to Williams et al., and are produced commercially, for example, by Tepha, Inc. (Lexington, Mass.). Poly(4-hydroxybutyrate) (P(4HB), TephaFLEX® biomaterial) is a strong, pliable thermoplastic polyester that, despite its biosynthetic route, has a relatively simple structure.

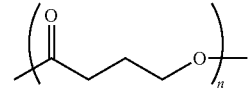

The polymer belongs to a larger class of materials called polyhydroxyalkanoates (PHAs) that are produced by numerous microorganisms (see, for example, Steinbüchel A., et al. Diversity of Bacterial Polyhydroxyalkanoic Acids, *FEMS Microbial. Lett.* 128: 219-228 (1995)). In nature these polyesters are produced as storage granules inside cells, and serve to regulate energy metabolism. They are also of commercial interest because of their thermoplastic properties, and relative ease of production. Several biosynthetic routes are currently known to produce P(4HB):

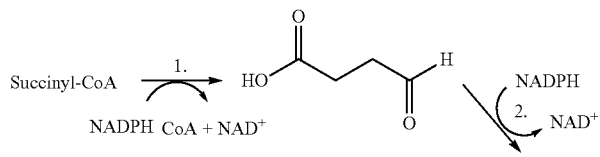

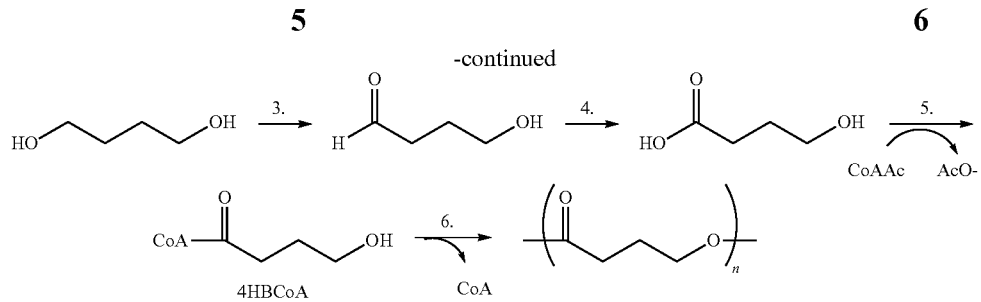

This schematic shows some of the known biosynthetic pathways for the production of P(4HB). Pathway enzymes are: 1. Succinic semialdehyde dehydrogenase, 2. 4-hydroxybutyrate dehydrogenase, 3. diol oxidoreductase, 4. aldehyde dehydrogenase, 5. Coenzyme A transferase and 6. PHA synthetase.

Chemical synthesis of P(4HB) has been attempted, but it has been impossible to produce the polymer with a sufficiently high molecular weight that is necessary for most applications (Hori, Y., et al., Polymer 36: 4703-4705 (1995)).

U.S. Pat. Nos. 6,245,537, 6,623,748 and 7,244,442 describe methods of making PHAs with little endotoxin, which is suitable for medical applications. U.S. Pat. Nos. 6,548,569, 6,838,493, 6,867,247, 7,268,205, and 7,179,883 describe use of PHAs to make medical devices. Copolymers of P(4HB) include 4-hydroxybutyrate copolymerized with 3-hydroxybutyrate or glycolic acid (U.S. patent application No. 20030211131 by Martin and Skraly, U.S. Pat. No. 6,316,262 to Huisman, et al., and U.S. Pat. No. 6,323,010 to Skraly, et al.). Methods to control molecular weight of PHA polymers have been disclosed in U.S. Pat. No. 5,811,272 to Snell, et al.

PHAs with controlled degradation and degradation in vivo of less than one year are disclosed in U.S. Pat. Nos. 6,548,569, 6,610,764, 6,828,357, 6,867,248, and 6,878,758 to Williams, et al. and WO 99/32536 to Martin, et al. Applications of P(4HB) have been reviewed in Williams, S. F., et al., *Polyesters, III*, 4: 91-127 (2002), and by Martin, D., et al. Medical Applications of Poly-4-hydroxybutyrate: A Strong Flexible Absorbable Biomaterial, *Biochem. Eng. J.* 16: 97-105 (2003).

Medical devices and applications of P(4HB) have also been disclosed by WO 00/56376 to Williams, et al. Several patents including U.S. Pat. Nos. 6,555,123, 6,585,994, and 7,025,980 describe the use of PHAs in tissue repair and engineering. WO 05/007195 to Hasirci, et al. describes P(4HB) matrices for sustained drug delivery, and WO 05/020825 describes P(4HB) nerve regeneration devices. WO 07/092418 and WO 10/017014 to Schmitz describe polymeric degradable drug-eluting stents and coatings, and WO 09/158724 to Markland describes injectable drug delivery systems using P(4HB) and copolymers thereof.

B. Physiologically Active Substances

The PHA polymers applied to the implantable stimulation devices may contain or be coated with physiologically active substances in order to provide controlled release of an active substance in vivo. In the case of an implantable cochlear device, the active substance would be released inside the inner ear.

The physiologically active substances can be selected according to the condition to be treated. For example, antibiotics can be selected to prevent infection. Trauma to tissues can be treated by selection of anti-inflammatory drugs and anti-proliferative agents, and anti-apoptosis agents can be used to control apoptosis. In addition, neurotrophic factors, gene therapy agents, anti-oxidants, and other active substances can be incorporated into the implantable stimulation device to prevent fibrous tissue formation, inflammation, infection, apoptosis and/or necrosis of nervous tissue, as well as to stimulate healing and improve the performance of the implantable stimulation device.

If desired, it is also possible to incorporate more than one physiologically active substance in the implantable stimulation device. For example, an anti-inflammatory agent and an antibiotic could be incorporated into the same device. Release rates may differ as a function of concentration, different chemical compositions, and different solubilities in vivo.

Preferred physiologically active substances are anti-inflammatory agents, anti-proliferative agents, anti-apoptosis agents, antibiotics, and other substances to prevent fibrous tissue formation and infection. Examples of preferred anti-inflammatory agents are steroids, such as dexamethasone, betamethasone, clobethasole, diflorasone, fluocinolone, triamcinolone, or any combination thereof. Examples of preferred anti-proliferative agents are limus drugs, such as Sirolimus.

CIPRODEX® Otic ((ciprofloxacin 0.3% and dexamethasone 0.1%) is indicated for the treatment of infections caused by susceptible isolates of the designated microorganisms in Acute Otitis Media in pediatric patients (age 6 months and older) with tympanostomy tubes due to *Staphylococcus aureus, Streptococcus pneumoniae, Haemophilus influenzae, Moraxella catarrhalis*, and *Pseudomonas aeruginosa*. ANTIBIOTIC® Ear; CORTISPORIN® contains neomycin 3.5 mg, polymyxin B 10,000 units, and hydrocortisone 10 mg per mL (10 mL). Ofloxacin (FLOXIN OTIC®) a quinolone antibiotic is used for chronic suppurative otitis media with perforated tympanic membranes. These drugs should be deliverable using this technology to reduce infection and/or inflammation.

The rate of release of the active physiological agent may be selected to control the specific condition being treated. In a preferred embodiment, the rate of release of dexamethasone during a 24-hour period is between 0.1 and 1.0 µg.

C. Other Components

The PHA polymers and copolymers may contain other materials, including plasticizers, nucleants, other polymers (including absorbable polymers), additives, dyes, and compatibilizers. Examples of plasticizers are disclosed by U.S Pat. No. 6,905,987 to Noda, et al. Other components may be added to impart benefits such as, but not limited to, increased lubricity, increased stability, including oxidative stability, color, flexibility, toughness, and resiliency. Other absorbable polymers that may be included in the compositions include those comprising the following monomers: glycolic acid, lactic acid, trimethylene carbonate, p-dioxanone, and caprolactone.

It may also be advantageous to incorporate contrast agents, radiopaque markers, or radioactive substances.

III. Methods of Manufacturing Implantable Stimulation Devices

Drug eluting implantable stimulation devices can be prepared by coating such devices with PHA polymers and drugs.

In a preferred embodiment, the implantable stimulation device is pre-treated in order to improve the adherence of the PHA polymer based local drug delivery system to the implantable stimulation device. A preferred method of pre-treating a cochlear implant is to activate the silicone surface. This can be achieved, for example, using low-pressure plasma. After treatment with plasma, the resulting surface may be derivatized with suitable polymers in order to enhance the adhesion of the PHA polymers to the implantable stimulation device.

After pre-treatment of the surface of the implantable stimulation device, if any, the PHA polymer drug delivery system can be applied to the device. In a preferred embodiment, the PHA polymer drug delivery system is applied to the implantable stimulation device by spray-coating. In a particularly preferred embodiment, the PHA polymer and the drug are dissolved in a solvent, and then spray-coated onto the implantable stimulation device. Alternatively, the PHA polymer solution containing the drug may be applied by dip coating. The preferred PHA polymers are P(4HB) and copolymers thereof. In a particularly preferred method, the P(4HB) and copolymers thereof, have weight average molecular weights between 50,000 and 800,000. The preferred solvents are chlorinated hydrocarbons, such as chloroform and methylene chloride, and other volatile solvents such as acetone. The amount of drug and PHA polymer applied to the surface of the implantable stimulation device may be varied to achieve the desired drug delivery profile.

Further optimization of the drug delivery profile can be achieved, by blending other polymers with the PHA polymer, particularly absorbable polymers, as well as by top coating the PHA polymer drug delivery system once it has been applied to the implantable stimulation device. For example, in a preferred embodiment, a cochlear implant coated with a PHA polymer containing a drug may be further coated (top coated) with polylactic acid. The latter may be applied by spray-coating, or dip coating.

Another promising way is to pre-treat the surface of the implantable stimulation device and link a polymeric undercoating (PHA polymers), as a primer, to the surface. Afterwards PHA coatings with incorporated drugs are applied to the CI by a spray-coating technique.

The present invention will be further understood by reference to the following non-limiting examples.

EXAMPLE 1

Measurement of Cell Viability Using Neutral Red Assay

Cell survival and viability of NIH-3T3 fibroblasts were measured using a Neutral Red Assay. NIH-3T3 fibroblasts were seeded into 96-well cell culture plates at a density of $10^4$ cells/well in Dulbecco's Modified Eagle's Medium supplemented with 10% fetal calf serum. After 48 hours, cells were stained using a Neutral Red Assay. Neutral red is taken up only by living cells.

After incubation for 3 hours and several washing steps, cells were permeabilized and the neutral red solubilized in the supernatant. The absorption measured at 570 nm is proportional to the number of living cells. Measurements were run in quintuplicate and results were averaged. The experiment was repeated at least four times.

EXAMPLE 2

Cell Adsorption and Quantification of Spiral Ganglion Cells By Antibody Staining and Microscopic Evaluation Spiral ganglion cells were freshly isolated from Sprague-Dawley rats (p3-5). Viable cells were suspended in Dulbecco's Modified Eagle's Medium supplemented with 10% fetal calf serum and 50 ng/ml BDNF and were seeded onto laminin- and ornithin-coated cell culture plates at a density of $1.5\times10^4$ cells/well. After a cultivation time of 48 hours, cells were stained with anti-neurofilament antibody and counted under a microscope. All experiments were performed in quadruplicate and the experiment was repeated four times.

EXAMPLE 3

In Vitro Survival of Fibroblasts and Spiral Ganglion Cells on P(4HB) and PLLA Versus Silicone In order to evaluate the potential use of P(4HB) and PLLA as drug carriers for implantable stimulation devices, the survival rates of fibroblasts and spiral ganglion cells on these two polymers were investigated.

Discs (0.1 mm thick and 6 mm in diameter) of poly(L-lactide) (PLLA, Resomer L214, Boehringer Ingelheim Pharma GmbH & Co. KG, Ingelheim, Germany), poly(4-hydroxybutyrate) (P(4HB), Tepha, Inc., Lexington, Mass., USA) and silicone were placed at the bottom of standard 96-well tissue culture plates. Microtiter plates without material additions served as controls. Cells were seeded into each of the different cell culture wells and the assays were carried out as described above in Examples 1 and 2. For absorption measurements when using NIH-3T3 cells and neutral red test, the supernatant of all wells was transferred into new wells after permeabilization of the cells. Surviving spiral ganglion cells were stained directly on the polymer discs and counted.

Figure 1:
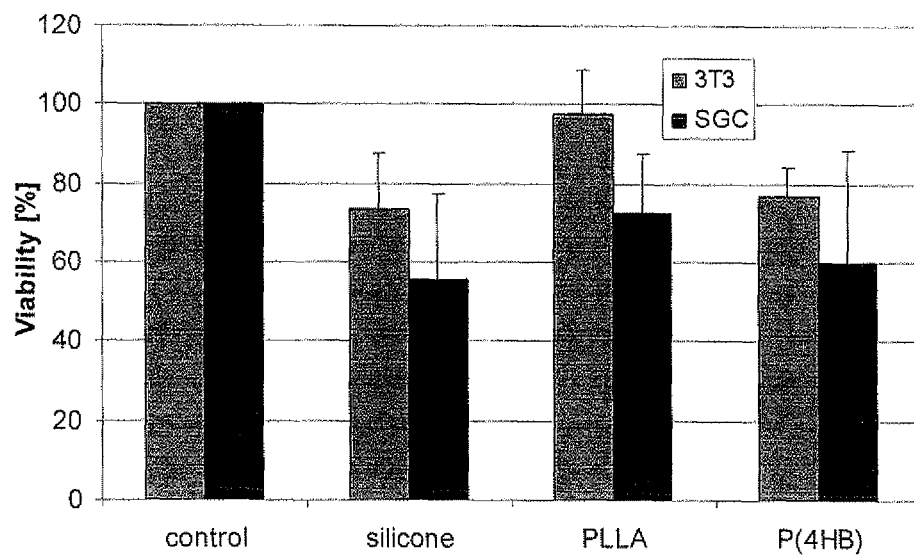
FIG. 1 is a graph of fibroblast (NIH-3T3) viability and spiral ganglion cell (SGC) survival on silicone and the biodegradable polymers PLLA or P(4HB).

The cell viability results relative to control (seeded cells on polystyrene-based cell culture plate material) are shown in FIG. 1. The fibroblast growth on P(4HB) was comparable to that on silicone whereas cell growth on PLLA was similar to that on cell culture plate material (FIG. 1). Experiments with freshly isolated spiral ganglion cells, showed no influence of the biodegradable polymers on cell survival in comparison to silicone. However, viability of the SGCs was reduced by 30 to 40% on all three polymers compared to cell culture plate material (FIG. 1).

These data show that NIH-3T3 fibroblasts grow as well on P(4HB) disks as on silicone. The viability of rat spiral ganglion cells grown on each material is comparable for all of the polymers tested.

EXAMPLE 4

Cell Viability and Survival of Fibroblasts and Neuronal Cells in the Presence of Dexamethasone and Sirolimus In order to evaluate the potential use of dexamethasone (DMS) and sirolimus (SIR) on implantable stimulation devices, the dose-dependent effect of these two drugs on viability of fibroblasts and spiral ganglion cells was investigated.

Figure 2:
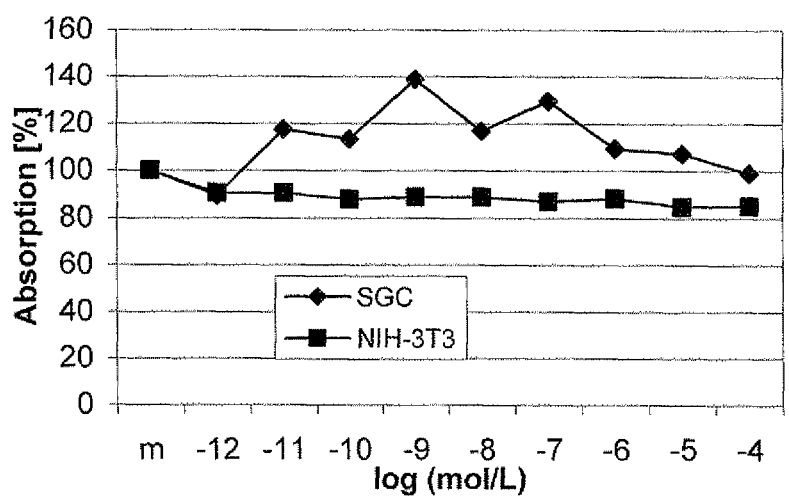
FIG. 2 is a graph of the effects of dexamethasone at concentrations between $1 \times 10^{-12}$ and $1 \times 10^{-4}$ mol/L on fibroblast (NIH-3T3) and spiral ganglion cell (SGC) viability.

The NIH-3T3 fibroblasts were cultured and assayed with Neutral Red according to Example 1, except that dexamethasone or sirolimus were added to the cell culture at concentrations between $10^{-12}$ and $10^{-4}$ mol/L. The percentage of viable NIH-3T3 cells was assayed relative to the control (no drug) and the results are shown in FIGS. 2 (dexamethasone) and 3 (sirolimus).

Spiral ganglion cells were isolated, cultured and quantified as described in Example 2, except that dexamethasone and sirolimus were added to the cell culture at concentrations between $10^{-12}$ and $10^{-4}$ mol/L. The percentage of viable SGC cells was assayed relative to the control (no drug) and the results are shown in FIG. 2 (dexamethasone) and FIG. 3 (sirolimus). Dexamethasone showed no toxic effects on NIH-3T3 cell and spiral ganglion cell viability at the concentrations and conditions tested. On the contrary, the presence of dexamethasone at concentrations between $10^{-11}$ to $10^{-7}$ mol/L resulted in approximately a 20% increase of spiral ganglion cell viability (FIG. 2).

Figure 3:
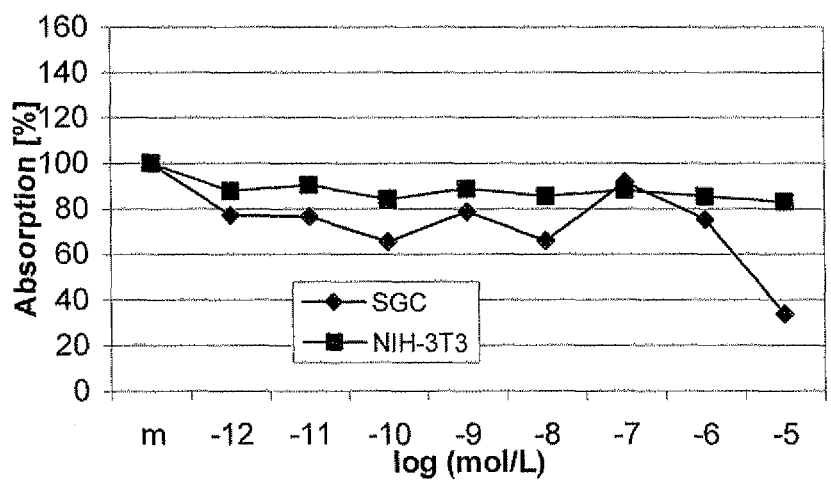
FIG. 3 is a graph of the effect of sirolimus on cultured NIH-3T3 fibroblasts and spiral ganglion cells (SGC). At a concentration of $10^{-5}$ mol/L survival of SGC was reduced.

Sirolimus exerts only a small decrease in NIH-3T3 cell viability in the concentration range tested. In contrast, at a high concentration of $10^{-5}$ mol/L, the viability of spiral ganglion cells was substantially reduced (FIG. 3).

These data show that the presence of dexamethasone or sirolimus at concentrations between $10^{-12}$ and $10^{-6}$ mol/L do not have an adverse impact on the viability of SGC and NIH-3T3 cells grown in cell culture.

EXAMPLE 5

Chemical Activation of Silicone as Material of the CI Electrode Carrier and Wet-chemical Application of PHA Polymer Undercoatings The silicone surface was activated using plasma-chemical processes and derivatized to improve PHA polymer adhesions as follows.

Prior to plasma-chemical activation the silicone (NuSil MED-4234, NuSil Technology Europe, Mougins, France) discs were rinsed with ethanol for cleaning. Plasma-chemical activations were run on a plasma system that was equipped with a 300 W radio frequency generator. Initially, the chamber was evacuated to a pressure of 0.09 mbar. Then an oxygen ($O_2$) pressure of 0.30 mbar was applied. The $O_2$ plasma was run for 1 min at 45% generator power. Afterwards the chamber was vented with air. Subsequently, the $O_2$ plasma activated silicone discs were immersed into a solution (10% v/v) of 3-aminopropyl-triethoxysilane (APTES) in ethanol. The discs were allowed to react at least 2 h at 50° C. Then, the chemically surface modified silicone discs were removed from solution, rinsed with ethanol and dried in vacuo at 40° C. Alternatively, reactive amino groups could be generated on the silicone surface using an $NH_3$ plasma.

In order to enhance the adhesion of the drug-containing polymer coatings to the silicone, an undercoating of the polymer P(4HB) was applied to the silicone surface. The chemical- or plasma-modified silicone surfaces from above were activated and bonded with P(4HB) by immersion of the silicone discs into a solution of N-hydroxysuccinimide, 1-[3-(dimethylamino)propyl]-3-ethylcarbodiimide hydrochloride (1.8 g/L) and P(4HB) (18.2 g/L) in 1,2-dichloroethane ($EtCl_2$) and shaken for 8 h at 55° C. Afterwards, the silicone samples were rinsed with $EtCl_2$ and dried in a vacuum drying cabinet at 40° C. for at least 16 h.

EXAMPLE 6

Coating of Silicone with PHA Polymer Drug Compositions

The drug-containing polymer coatings were applied to silicone fibers using a spray-coating device manufactured by the IIB e.V. (Institute for Implant Technology and Biomaterials, Rostock-Warnemünde, Germany). Spray solutions contained 2.3 g/L of P(4HB) in 1,2-dichloroethane. To the polymer solution a solution of dexamethasone in methanol (15 g/L) was added to give a polymer to dexamethasone ratio of 70/30 or 85/15 (% w/w). To each fiber a polymer/drug coating with an absolute mass of ~225 µg was applied. The fibers were dried in a desiccator for at least 24 h at 40° C. The mass of the polymer/drug coating was determined by use of a MettlerToledo UMX 5 Ultra-micro Balance.

Environmental Scanning Electron Microscopy (ESEM) studies of the polymer coated silicone fibers showed the P(4HB) coated fiber to have a smoother surface appearance than the uncoated silicone fiber.

EXAMPLE 7

In vitro Drug Release from PHA Polymer Drug Coatings Under Quasi-stationary Conditions In order to evaluate the in vitro release of dexamethasone from P(4HB)/DMS coatings, in vitro drug release studies were performed using a quasi-stationary release model for simulation of the inner ear conditions.

A DMS containing P(4HB) coated silicone disc (prepared as described in Example 6) was placed in a capped glass vial containing 500 of isotonic sodium chloride (NaCl, 0.9%) as the elution medium. The vial was placed into an oven at 37° C. without agitation. After a designated period of time, 100 µL of the elution medium was removed from the vial and subjected to HPLC analysis over a Chromolith® FastGradient RP-18e 50-2 column. To perform the chromatography, a mixture (50/50% v/v) of methanol and ultra pure water ($\sigma$=0.05 µS/cm at 25° C.) was run isoeratically at 23° C. as mobile phase. Flow rate was 0.4 mL/min and detection wavelength was set to 254 nm. Standards of dexamethasone were used with concentrations of 0.1, 0.5, 1.0, 2.0, 5.0 and 10 µg/mL for calibration. Another 100 µL of isotonic NaCl solution were given into the glass vial for refilling the elution medium and the vial was placed into the oven again. Samples were removed and analyzed as above over 400 hours. In the first 24 h, the P(4HB)-DMS coatings showed a distinct burst release wherein 35 to 40 µg of the embedded DMS were released. Since the amount of drug contained in the coating with 15% of DMS was nearly exhausted after this time, the later drug release was minimal for this coating. In contrast, the higher loaded P(4HB) coating (30% of DMS) showed a continued release beyond the initial burst release phase extending to at least 120 h before the drug was exhausted (FIG. 4).

These data show a prolonged release profile of DMS from the P(4HB)/DMS coating, and that all the drug is released from the coating.

EXAMPLE 8

Simulated Implantation of PHA Polymer Drug Coated CI

In order to evaluate the adhesion and mechanical stability of P(4HB)/DMS coatings on the silicone-based electrode carrier of the CI the implantation process was simulated using a human explant of the petrous part of the temporal bone.

For the simulated implantation, CI Nucleus® 24 Contour Advance™ Practice Electrodes (Cochlear Ltd, Lane Cove, NSW, Australia) were used. A 200 µg polymer coating containing P(4HB)/DMS 85/15 (% w/w) was applied to the implant. The coated CI was introduced into the tympanic cavity and inserted into the cochlea through the round window. Subsequently, the CI was removed. The surface morphology was inspected before and after the implantation process by ESEM. The simulated implantation procedure did not damage the P(4HB)/DMS 85/15 (% w/w) coating on the CI. ESEM examination showed that the coating completely covered the CI before and after the simulated implantation procedure. After the implantation some contamination is visible on the surface, but apart from some small wrinkles in the P(4HB) coating, the coating remained intact.

These data show that the P(4HB)/DMS coating is robust and remains intact during a simulated implantation procedure.

EXAMPLE 9

Chemical Activation of DMS-containing Silicone as Material of the CI Electrode Carrier and Wet-chemical Application of PHA Polymer Undercoatings The silicone surface was activated using plasma-chemical processes and derivatized to improve PHA polymer adhesions as follows.

Prior to plasma-chemical activation the DMS-containing silicone (NuSil MED-4234, NuSil Technology Europe, Mougins, France) discs were rinsed with ethanol for cleaning. Plasma-chemical activations were run on plasma system that was equipped with a 300 W radio frequency generator. Initially, the chamber was evacuated to pressure of 0.09 mbar. Then an ammonia ($NH_3$) pressure of 0.3 mbar was applied. The $NH_3$ plasma was run for 1 min at 15% generator power. Afterwards the chamber was vented with air. In order to enhance the adhesion of the drug-containing polymer coatings to the DMS-loaded silicone, an undercoating of the polymer P(4HB) was applied to the silicone surface. The plasma-modified silicone surfaces from above were activated and bonded with P(4HB) by immersion of the silicone discs into a solution of N-hydroxysuccinimide, 1-[3-(dimethylamino)propyl]-3-ethylcarbodiimide hydrochloride (1.8 g/L) and P(4HB) (18.2 g/L) in $EtCl_2$ and shaken for 5 min at 55° C. Afterwards, the silicone samples were rinsed with $EtCl_2$ and dried in a vacuum drying cabinet at 40° C. for at least 16 h.

EXAMPLE 10

In vitro Drug Release from DMS-containing Silicone Carriers with PHA Polymer Drug Coatings Under Quasi-stationary Conditions In order to evaluate the in vitro drug release from DMS-containing silicone carriers equipped with P(4HB)/DMS coatings, in vitro drug release studies were performed using a quasi-stationary release model for stimulation of the inner ear conditions.

The in vitro drug release is carried out as described in Example 7 for a period of 45 days. In the first 24 h, the DMS-containing silicone carrier with P(4HB)-DMS coatings showed a distinct burst release wherein 34 to 48 µg of the incorporated DMS were released.

The silicone carriers with 1% DMS was nearly exhausted after the initial burst release phase, while the silicone carriers containing 5% DMS showed a continued release beyond the initial burst release phase extending to at least 45 days. In each case the absolute released DMS amount mainly depends on the composition of the P(4HB)/DMS coatings (FIG. 5).

EXAMPLE 11

Biofunctionalization of Silicone Carriers Containing PHA Polymer Drug Coatings

Silicone carriers containing P(4HB) polymer drug coatings were activated using plasma-chemical processes and further functionalized with a nerve growth factor, such as brain-derived neurotrophic factor (BDNF).

Prior to plasma-chemical activation the DMS containing P(4HB) coated silicone discs (prepared as described in Example 6) were rinsed with ethanol for cleaning. Plasma-chemical activations were run on plasma system that was equipped with a 300 W radio frequency generator. Initially, the chamber was evacuated to pressure of 0.09 mbar. Then an ammonia ($NH_3$) pressure of 0.3 mbar was applied. The $NH_3$ plasma was run for 3 min at 60% generator power. Afterwards the chamber was vented with air. Alternatively, reactive oxygen groups could be generated using $O_2$ plasma (6 min at 40% generator power). The resulting activated DMS containing P(4HB) coated silicone discs were placed in a capped glass vial containing 4 mL BDNF (1000 ng/L) in Diluent B (RayBio®, Human BDNF ELISA Kit). The discs were shaken for 16 h at 4° C. Afterwards the silicone samples were rinsed with a solution of Tween 20 (0.05% (w/w)) in phosphate buffered saline and stored at −20° C. The BDNF-content on the P(4HB) coated silicone discs were quantified using an enzyme-linked immunosorbent assay (RayBio®, Human BDNF ELISA Kit).

We claim:
1. An implantable neural stimulation device comprising an outermost layer of a poly-4-hydroxybutyrate (P4HB) polymer-drug layer applied to-a plasma-activated silicone surface, wherein the P4HB-drug layer is smoother than the silicone surface, as measured by environmental Scanning electron microscopy.
2. The device of claim 1, wherein a poly-4-hydroxybutyrate (P4HB) polymer undercoating is coated onto the silicone surface.
3. The device of claim 1 wherein the drug is selected from the group comprising anti-inflammatory agents, anti-proliferative agents, anti-apoptosis agents, antibiotics, neurotrophic factors, and gene therapy agents.
4. The device of claim 3 wherein the drug is dexamethasome or sirolimus.
5. The device of claim 1 wherein the polymer-drug layer comprises polylactic acid.
6. The device of claim 1 wherein the device is a cochlear implant.
7. The device of claim 1 wherein the drug is delivered locally for at least three days following implantation.
8. A method of producing an implantable stimulation device comprising providing a plasma activated silicone surface of the implantable stimulation device, and
applying a P4HB polymer solution containing a drug onto the silicone surface to form a P4HB-drug layer as the outermost layer, wherein the P4HB-drug layer is smoother than the silicone surface, as measured by environmental Scanning electron microscopy.

9. A method of using the device of claim 1 comprising implanting the device at a site in the patient in need thereof.

10. The device of claim 1, wherein the P4HB polymer is activated so that it is covalently bound to the silicone surface.

11. The method of claim 8, wherein the P4HB polymer is activated so that it is covalently bound to the silicone surface.

12. The device of claim 2 wherein the coating comprising drug and P4HB polymer is applied to the P4HB polymer undercoating by spray-coating or dip coating.

13. The method of claim 8, comprising applying a P4HB polymer undercoating onto the plasma activated silicone surface.

* * * * *

UNITED STATES PATENT AND TRADEMARK OFFICE
CERTIFICATE OF CORRECTION

| | | |
|---|---|---|
| PATENT NO. | : 9,162,010 B2 | Page 1 of 1 |
| APPLICATION NO. | : 13/284287 | |
| DATED | : October 20, 2015 | |
| INVENTOR(S) | : Lenarz et al. | |

It is certified that error appears in the above-identified patent and that said Letters Patent is hereby corrected as shown below:

In the claims
Claim 1, column 12, line 41, replace "to-a" with --to a--.

Signed and Sealed this
First Day of March, 2016

Michelle K. Lee
*Director of the United States Patent and Trademark Office*